US008299299B2

(12) United States Patent
Blum et al.

(10) Patent No.: US 8,299,299 B2
(45) Date of Patent: Oct. 30, 2012

(54) PROCESS FOR SEPARATING ACRYLIC ACID PRESENT AS A MAIN CONSTITUENT AND GLYOXAL PRESENT AS A BY-PRODUCT IN A PRODUCT GAS MIXTURE OF A PARTIAL HETEROGENEOUSLY CATALYZED GAS PHASE OXIDATION OF A C3 PRECURSOR COMPOUND OF ACRYLIC ACID

(75) Inventors: Till Blum, Kuantan (MY); Peter Zurowski, Landau (DE); Steffen Rissel, Kirchheim (DE); Sylke Haremza, Neckargemuend (DE); Thorsten Friese, Mannheim (DE); Ulrich Jaeger, Roemerberg (DE); Volker Schliephake, Schifferstadt (DE); Klaus Joachim Mueller-Engel, Stutensee (DE); Ulrich Hammon, Mannheim (DE); Joerg Heilek, Bammental (DE); Imke Britta Mueller, Heidelberg (DE)

(73) Assignee: BASF SE, Ludwigshafen (DE)

( * ) Notice: Subject to any disclaimer, the term of this patent is extended or adjusted under 35 U.S.C. 154(b) by 565 days.

(21) Appl. No.: 12/509,078

(22) Filed: Jul. 24, 2009

(65) Prior Publication Data
US 2010/0022734 A1 Jan. 28, 2010

Related U.S. Application Data

(60) Provisional application No. 61/084,109, filed on Jul. 28, 2008, provisional application No. 61/091,900, filed on Aug. 26, 2008.

(30) Foreign Application Priority Data

Jul. 28, 2008 (DE) .......................... 10 2008 040 799
Aug. 26, 2008 (DE) .......................... 10 2008 041 573

(51) Int. Cl.
 *C07C 51/42* (2006.01)
(52) U.S. Cl. ...................................... 562/600
(58) Field of Classification Search .................. None
 See application file for complete search history.

(56) References Cited

U.S. PATENT DOCUMENTS

| 4,317,926 | A | 3/1982 | Sato et al. |
| 5,198,578 | A | 3/1993 | Etzkorn et al. |
| 6,433,222 | B1 | 8/2002 | Eck et al. |
| 6,448,439 | B1 | 9/2002 | Eck et al. |
| 7,589,236 | B2 | 9/2009 | Heilek et al. |
| 2004/0242826 | A1 | 12/2004 | Nishimura |
| 2006/0199976 | A1 | 9/2006 | Heilek et al. |
| 2009/0076232 | A1* | 3/2009 | Heilek et al. ............ 526/77 |

FOREIGN PATENT DOCUMENTS

| DE | 26 06 364 | | 9/1977 |
| DE | 43 08 087 A1 | | 9/1994 |
| DE | 43 35 172 A1 | | 4/1995 |
| DE | 44 36 243 A1 | | 4/1996 |
| DE | 195 01 325 A1 | | 7/1996 |
| DE | 196 06 877 A1 | | 8/1997 |
| DE | 196 27 847 A1 | | 1/1998 |
| DE | 198 35 247 A1 | | 2/1999 |
| DE | 197 40 252 A1 | | 3/1999 |
| DE | 197 40 253 A1 | | 3/1999 |
| DE | 198 37 520 A1 | | 2/2000 |
| DE | 100 53 086 | | 10/2000 |
| DE | 199 24 532 A1 | | 11/2000 |
| DE | 199 24 533 A1 | | 11/2000 |
| DE | 101 15 277 A1 | | 6/2002 |
| DE | 101 22 787 A1 | | 6/2002 |
| DE | 101 31 297 A1 | | 1/2003 |
| DE | 102 35 847 A1 | | 8/2003 |
| DE | 102 23 058 A1 | | 12/2003 |
| DE | 103 36 386 A1 | | 3/2004 |
| DE | 102 43 625 A1 | | 4/2004 |
| DE | 102 45 585 A1 | | 4/2004 |
| DE | 102 46 119 A1 | | 4/2004 |
| DE | 102 47 240 A1 | | 4/2004 |
| DE | 103 32 758 A1 | | 5/2004 |
| DE | 10 2005 052 917 A1 | | 10/2007 |
| DE | 10 2007 019 597 A1 | | 5/2008 |
| DE | 10 2007 043 748 A1 | | 9/2008 |
| DE | 10 2007 043 759 A1 | | 9/2008 |
| DE | 10 2007 043 758 A1 | | 10/2008 |
| DE | 10 2007 055 086 A1 | | 5/2009 |
| EP | 0 117 146 A1 | | 8/1984 |
| EP | 0 608 838 A2 | | 8/1994 |
| EP | 0 616 998 A1 | | 9/1994 |
| EP | 0 648 520 A1 | | 4/1995 |
| EP | 0 695 736 A1 | | 2/1996 |
| EP | 0 770 592 A1 | | 5/1997 |
| EP | 0 776 875 A1 | | 6/1997 |
| EP | 0 778 255 A1 | | 6/1997 |
| EP | 0 792 867 A2 | | 9/1997 |
| EP | 0 854 129 A1 | | 7/1998 |

(Continued)

OTHER PUBLICATIONS

Yunqing Chen et al., "Wavelength-Dependent Photolysis of Glyoxal in the 290-420 nm Region", Journal of Physical Chemistry A, © 2003 American Chemical Society, vol. 107, Issue 23, pp. 4643-4651.

J. P. Guette, et al. "Le Glyoxal, une Molécule Trés Fonctionnelle . . . " I. Préparations, Propriétés, L'actualité Chimique, May 1982, pp. 23-31.

*Primary Examiner* — Paul A Zucker

(74) *Attorney, Agent, or Firm* — Oblon, Spivak, McClelland, Maier & Neustadt, L.L.P.

(57) ABSTRACT

A process for separating acrylic acid present as a main product and glyoxal present as a by-product in a product gas mixture of a partial gas phase oxidation of a $C_3$ precursor compound, in which a liquid phase P is obtained, which consists of acrylic acid to an extent of at least 70% of its weight and, based on the molar amount of acrylic acid present therein, comprises at least 200 molar ppm of glyoxal, in which the glyoxal is separated from the acrylic acid in the liquid phase P by crystallization.

48 Claims, No Drawings

FOREIGN PATENT DOCUMENTS

| | | |
|---|---|---|
| EP | 0 920 408 | 6/1999 |
| EP | 0 982 287 A1 | 3/2000 |
| EP | 0 982 288 A2 | 3/2000 |
| EP | 0 982 289 A2 | 3/2000 |
| EP | 0 990 636 A1 | 4/2000 |
| EP | 1 015 410 | 7/2000 |
| EP | 1 015 411 | 7/2000 |
| EP | 1 041 062 A2 | 10/2000 |
| EP | 1 066 239 | 1/2001 |
| EP | 1 066 240 | 1/2001 |
| EP | 1 066 293 | 1/2001 |
| EP | 1 068 174 | 1/2001 |
| EP | 1 116 709 A1 | 7/2001 |
| EP | 1 125 912 A2 | 8/2001 |
| EP | 1 159 249 | 12/2001 |
| EP | 1 163 201 | 12/2001 |
| EP | 1 189 861 | 3/2002 |
| EP | 1 298 120 A2 | 9/2002 |
| EP | 1 252 129 | 10/2002 |
| EP | 1 298 120 A2 | 4/2003 |
| EP | 1 388 532 A1 | 2/2004 |
| EP | 1 388 533 A1 | 2/2004 |
| EP | 1 396 484 A1 | 3/2004 |
| EP | 1 484 303 A2 | 12/2004 |
| EP | 1 484 308 A1 | 12/2004 |
| EP | 1 484 309 A1 | 12/2004 |
| EP | 1 554 234 | 7/2005 |
| WO | WO 98/01414 A1 | 1/1998 |
| WO | WO 98/01415 A1 | 1/1998 |
| WO | WO 99/14181 A1 | 3/1999 |
| WO | WO 99/14182 A1 | 3/1999 |
| WO | WO 99/50219 A1 | 10/1999 |
| WO | WO 99/50220 A1 | 10/1999 |
| WO | WO 99/50222 A1 | 10/1999 |
| WO | WO 99/50269 A2 | 10/1999 |
| WO | WO 00/53560 A1 | 9/2000 |
| WO | WO 00/53561 A1 | 9/2000 |
| WO | WO 00/75097 A1 | 12/2000 |
| WO | WO 01/55076 A2 | 8/2001 |
| WO | WO 01/77056 A1 | 10/2001 |
| WO | WO 01/96270 A2 | 12/2001 |
| WO | WO 01/96271 A2 | 12/2001 |
| WO | WO 02/09839 A1 | 2/2002 |
| WO | WO 02/055469 A1 | 7/2002 |
| WO | WO 02/090310 A1 | 11/2002 |
| WO | WO 03/011804 A2 | 2/2003 |
| WO | WO 03/041832 A1 | 5/2003 |
| WO | WO 03/041833 A1 | 5/2003 |
| WO | WO 03/078378 A1 | 9/2003 |
| WO | WO 2004/007405 A1 | 1/2004 |
| WO | WO 2004/035514 A1 | 4/2004 |
| WO | WO 2004/063138 A1 | 7/2004 |
| WO | WO 2005/042459 A1 | 5/2005 |
| WO | WO 2005/047224 A1 | 5/2005 |
| WO | WO 2005/047226 A1 | 5/2005 |
| WO | WO 2005/073160 A1 | 8/2005 |
| WO | WO 2006/092272 A2 | 9/2006 |
| WO | WO 2006/114506 A1 | 11/2006 |
| WO | WO 2006/136336 A2 | 12/2006 |
| WO | WO 2007/006370 A1 | 1/2007 |
| WO | WO 2007/090991 A2 | 8/2007 |
| WO | WO 2008/090190 A1 | 7/2008 |

* cited by examiner

PROCESS FOR SEPARATING ACRYLIC ACID PRESENT AS A MAIN CONSTITUENT AND GLYOXAL PRESENT AS A BY-PRODUCT IN A PRODUCT GAS MIXTURE OF A PARTIAL HETEROGENEOUSLY CATALYZED GAS PHASE OXIDATION OF A C3 PRECURSOR COMPOUND OF ACRYLIC ACID

CROSS REFERENCE TO RELATED APPLICATIONS

This application claims the benefit of priority under 35 U.S.C. 119(e) to U.S. provisional applications 61/084109, filed July 28, 2008, and 61/091900, filed August 26, 2008. This application further claims the benefit of priority under 35 U.S.C. 119 to German applications 10 2008 040 799.2, filed Jul. 28, 2008, and 10 2008 041 573.1, filed Aug. 26, 2008.

The present invention relates to a process for separating acrylic acid present as a main product and glyoxal present as a by-product in a product gas mixture of a partial heterogeneously catalyzed gas phase oxidation of a $C_3$ precursor compound of acrylic acid, in which a liquid phase P is obtained which consists of acrylic acid to an extent of at least 70% of its weight and, based on the molar amount of acrylic acid present therein, comprises at least 200 molar ppm of glyoxal.

Acrylic acid is an important monomer which finds use as such and/or in the form of its alkyl esters for obtaining polymers used in the hygiene sector (for example water-superabsorbing polymers) (cf., for example WO 02/055469 and WO 03/078378).

Acrylic acid can be prepared in the gas phase, for example, by heterogeneously catalyzed partial oxidation of a $C_3$ precursor compound (e.g. propylene, propane, acrolein, propionaldehyde, propionic acid, propanol and/or glycerol) (cf., for example, EP-A 990 636, U.S. Pat. No. 5,198,578, EP-A 1 015 410, EP-A 1 484 303, EP-A 1 484 308, EP-A 1 484 309, US-A 2004/0242826 and WO 2006/136336).

In principle, in the course of such a heterogeneously catalyzed partial gas phase oxidation, pure acrylic acid is not obtained, but rather merely a product gas mixture which comprises acrylic acid and, as well as acrylic acid, also comprises constituents other than acrylic acid, from which the acrylic acid has to be removed.

Both the type and the quantitative proportion of the constituents other than acrylic acid in the product gas mixture can be influenced by factors including the purity of the $C_3$ precursor compound used as a raw material and the reaction conditions under which the heterogeneously catalyzed partial gas phase oxidation is carried out (cf., for example, DE-A 101 31 297 and DE-A 10 2005 052 917).

EP-A 770 592 discloses that the product gas mixture of such a heterogeneously catalyzed partial gas phase oxidation may comprise, among other compounds, various aldehydes as constituents other than acrylic acid. EP-A 770 592 also discloses that very small amounts of aldehydic impurities remaining in acrylic acid can significantly impair the properties of the acrylic acid. For instance, according to the teaching of EP-A 770 592, the individual aldehyde fractions within acrylic acid should be below 1 ppm in order to achieve the optimal product qualities in the course of use of such acrylic acid especially in free-radical polymerization reactions for, for example, production of superabsorbent polymers or of polymers effective as dispersants for oil drilling mud or as flocculants. In order to achieve these separations, EP-A 770 592 recommends the additional use of aldehyde scavengers. However, the additional requirement therefor simultaneously constitutes the disadvantage of the procedure recommended in EP-A 770 592.

EP-A 1 298 120 discloses that a possible by-product of a heterogeneously catalyzed partial gas phase oxidation of $C_3$ precursors which can be formed under particular conditions is also the aldehyde glyoxal. For reasons including the fact that glyoxal promotes the undesired free-radical polymerization of acrylic acid, EP-A 1 298 120 recommends configuring the acrylic acid preparation such that the glyoxal by-product formation is minimized (one possible source for glyoxal by-product formation in the course of a heterogeneously catalyzed partial gas phase oxidation of $C_3$ precursors of acrylic acid stated by EP-A 1 298 120 is the $C_2$ impurity ethylene which is possibly present in the $C_3$ precursor).

With additional use of reverse osmosis separation processes, according to EP-A 1 298 120, it is possible to obtain product gas mixtures from which the acrylic acid, even in the case of circulation of the absorbent, can be transferred to liquid phases which comprise less than 100 ppm by weight of glyoxal. According to the teaching of EP-A 1 298 120, the acrylic acid can subsequently be removed from such liquid phases in a comparatively problem-free manner by means of distillative separation processes. However, a disadvantage of this procedure is the requirement for reverse osmosis, which reduces the space-time yield.

EP-A 1 396 484 discloses a procedure, different than the method recommended in EP-A 1 298 120, for separating acrylic acid present as a main product and glyoxal present as a by-product in a product gas mixture of a partial heterogeneously catalyzed gas phase oxidation of a $C_3$ precursor compound of acrylic acid, which tolerates higher by-product contents of glyoxal (among other reasons, this is advantageous in that it permits the use of economically more attractive $C_3$ precursor compounds having an increased impurity content).

In this procedure, the acrylic acid and the glyoxal are absorbed from the product gas mixture initially into an aqueous solution.

The water is subsequently removed from this solution by azeotropic distillation (rectification). In order to substantially suppress undesired polymer formation, the procedure should be such that the reflux liquid has certain water contents and the reflux ratio does not go below a certain value.

In addition, particular temperature conditions have to be maintained.

Under these boundary conditions, the glyoxal accumulates in the form of high-boiling hydrates together with the acrylic acid in the column bottom.

The acrylic acid can subsequently be removed by distillation from the glyoxal hydrates in the aforementioned bottoms liquid, in which case the glyoxal hydrates quite obviously no longer have, or at worst have only to a significantly reduced degree, the quality of monomeric glyoxal of promoting the undesired free-radical polymerization of acrylic acid.

In-house studies by the applicant have shown that the ability of glyoxal, as an impurity in acrylic acid, to promote the tendency of acrylic acid to undesired free-radical polymerization, is significantly more pronounced compared to other possible by-product aldehydes of a heterogeneously catalyzed partial gas phase oxidation of $C_3$ precursor compounds (for example acetaldehyde, formaldehyde, propionaldehyde, benzaldehyde, butyraldehyde, acrolein), based on equal molar impurity contents. The reason for this is presumably that, as has been found as a result of quantum-mechanical calculations of dissociation energies, the thermal requirement for splitting of monomeric glyoxal into two formyl radicals is firstly particularly low, and the resulting formyl radicals are secondly much more reactive than, for example, a hydrogen radical or a methyl radical (CCSD(T) method (Coupled Cluster including Single, Double (and Triple) excitations)).

Experiments in connection with literature studies (e.g. L'actualité chimique, May 1982, pages 23 to 31, and the literature cited within this article) have confirmed that hydrates of glyoxal no longer have the aforementioned pronounced polymerization-promoting action of monomeric (molecular) glyoxal.

The glyoxal hydrates form two groups of hydrate types.

The first group consists of the monomeric glyoxal monohydrate and of the monomeric glyoxal dihydrate:

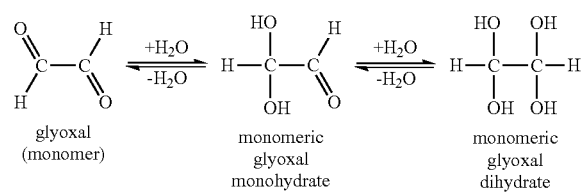

Both of the above glyoxal hydrates form even under comparatively mild conditions (relatively low temperatures, limited water contents are sufficient).

However, both the formation reactions of the monomeric glyoxal monohydrate and of the monomeric glyoxal dihydrate are markedly reversible reactions. In other words, neither of the two above hydrates any longer possesses the marked polymerization-promoting action of monomeric glyoxal, but monomeric glyoxal can reform from each of these hydrates, for example in the case of a moderate temperature increase, and are then capable in a manner known per se of promoting the undesired free-radical polymerization of acrylic acid. Hereinafter and quite generally in this document (apart from its preamble), the isolated term "glyoxal" shall therefore always be understood to comprise the total amount of monomeric glyoxal, monomeric glyoxal monohydrate and monomeric glyoxal dihydrate.

Against the background of the above, formation of monomeric glyoxal monohydrate and/or monomeric glyoxal dihydrate in the rectification column in the azeotropic distillation may therefore be insufficient for a successful implementation of the teaching given in EP-A 1 396 484, even though these hydrates normally have an elevated boiling point and are normally enriched in the column bottom together with acrylic acid.

For a successful implementation of the procedure recommended in EP-A 1 396 484, according to in-house studies, the formation of the hydrates of "polyglyoxal" or "oligoglyoxal" is instead required. They form the second group of glyoxal hydrates. Diglyoxal hydrates and triglyoxal hydrates are shown by way of example below:

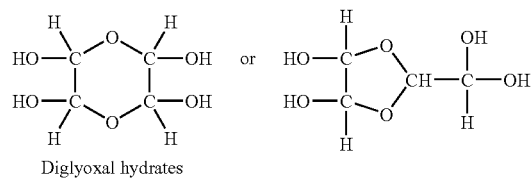

Diglyoxal hydrates

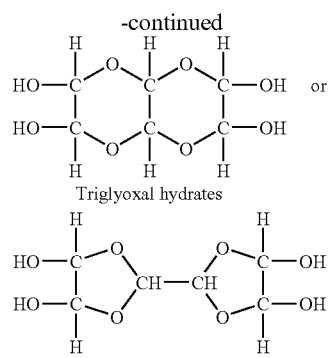

Triglyoxal hydrates

It is suspected that the formation of the polyglyoxal hydrates proceeds via the monomeric glyoxal dihydrate as an intermediate.

In contrast to the formation of the monomeric glyoxal hydrates, the formation of the polyglyoxal hydrates requires elevated temperatures (they are generally formed to a significant degree only at temperatures above 50° C.) and/or longer reaction times. Just like the monomeric glyoxal hydrates, the polyglyoxal hydrates also no longer have, or still have to a significantly lesser degree than monomeric glyoxal, at worst the polymerization-promoting tendency for acrylic acid which is typical of monomeric glyoxal. In contrast to the formation of the monomeric glyoxal hydrates, the polyglyoxal hydrates are, however, formed substantially irreversibly (at least under those conditions which are normally employed to remove acrylic acid from the product gas mixture of a heterogeneously catalyzed partial gas phase oxidation of a $C_3$ precursor compound of acrylic acid).

A successful application of the procedure recommended in EP-A 1 396 484 is thus comprehensible only on the basis of the formation of polyglyoxal hydrates. However, this requires, in a disadvantageous manner, both elevated temperatures and increased residence times.

It was therefore an object of the present invention to provide a process, improved over the process of the closest prior art, for separating acrylic acid present as a main product and glyoxal present as a by-product in a product gas mixture of a partial heterogeneously catalyzed gas phase oxidation of a $C_3$ precursor compound of acrylic acid, which essentially no longer has the disadvantages described in the prior art processes and more particularly does not require formation of polyglyoxal hydrates.

Accordingly, a process has been provided for separating acrylic acid present as a main product and glyoxal present as a by-product in a product gas mixture of a partial heterogeneously catalyzed gas phase oxidation of a $C_3$ precursor compound of acrylic acid, in which a liquid phase P is obtained which consists of acrylic acid to an extent of at least 70% of its weight and, based on the amount of acrylic acid present therein, comprises at least 200 molar ppm of glyoxal (this is understood in this document, as already stated, to mean the total amount of monomeric glyoxal, monomeric glyoxal monohydrate and monomeric glyoxal dihydrate), which comprises separating the glyoxal from the acrylic acid in the liquid phase P by crystallization, the acrylic acid being enriched in the crystals formed and the glyoxal in the mother liquor which remains in the course of crystallization.

One reason for the advantage of the process according to the invention is that it does not require any quantitative restriction in the glyoxal by-product formation, and another is that it does not require the formation of polyglyoxal hydrates.

It is additionally surprising that the depletion coefficient $A^{Gly}$ of glyoxal which is associated with the inventive crystallizative separation generally achieves values above ten thousand (>>10 000).

The depletion coefficient A is generally understood to mean the quantitative ratio of impurity remaining in the mother liquor to impurity remaining in the crystals (in each case expressed as % by weight based on the total amount of mother liquor or the total amount of crystals; for example, centrifugation or centrifugation and/or washing allows mother liquor and crystals to be essentially fully separated from one another and subsequent analysis allows the depletion coefficient A to be determined; a removal of mother liquor to an extent of more than 90% by weight, preferably to an extent of more than 95, or 97 or 98, or 99% by weight of the total amount thereof is generally sufficient for this purpose).

No other undesired possible by-product of the heterogeneously catalyzed partially oxidative preparation of acrylic acid from the $C_3$ precursor compounds thereof in the gas phase achieves an A value of comparable size in the course of a corresponding crystallizative separation.

This fact is all the more surprising in that $A^{Gly}$ includes not just the crystallizative removal of monomeric glyoxal but the crystallizative removal of monomeric glyoxal, monomeric glyoxal monohydrate and monomeric glyoxal dihydrate (cf. definition of the isolated term "glyoxal").

The above finding opens up the possibility, on the route to, for example, superabsorbent-grade glacial acrylic acid, of removing the glyoxal impurities which obstruct such a use in a single separation step, in a single crystallization stage, from a liquid phase P in a satisfactory manner.

The unit "molar ppm" should be understood such that, when a particular amount of liquid phase P comprises, for example, 1 mol of acrylic acid and the same amount of liquid phase P simultaneously comprises $10 \cdot 10^{-6}$ mol of glyoxal, 10 molar ppm of glyoxal are present in this amount of liquid phase P based on the molar amount of acrylic acid present therein.

In other words, the process according to the invention can also be employed successfully when the liquid phase P which consists of acrylic acid to an extent of at least 70% of its weight, based on the molar amount of acrylic acid present therein, comprises $\geq 250$ molar ppm, or $\geq 300$ molar ppm, or $\geq 400$ molar ppm, or $\geq 500$ molar ppm, or $\geq 750$ molar ppm, or $\geq 1000$ molar ppm, or $\geq 1250$ molar ppm, or $\geq 1500$ molar ppm of glyoxal (in this document, this is the total amount of monomeric glyoxal, monomeric glyoxal monohydrate and monomeric glyoxal dihydrate).

In general, the liquid phase P, which consists of acrylic acid to an extent of at least 70% of its weight, based on the molar amount of acrylic acid present therein, will comprise $\leq 5$ mol %, frequently $\leq 2$ mol %, or $\leq 1$ mol %, of glyoxal. Of course, the process according to the invention can also be employed successfully in the case of the above glyoxal contents.

The process according to the invention can, however, be employed successfully for all glyoxal contents (i.e. each individual glyoxal content, including those mentioned above) of the liquid phase P specified individually in this document (reported in each case in molar ppm based on the molar amount of acrylic acid present in the liquid phase P) when the liquid phase P consists of acrylic acid to an extent of $\geq 75\%$ by weight, or to an extent of $\geq 80\%$ by weight, or to an extent of $\geq 85\%$ by weight, or to an extent of $\geq 90\%$ by weight, or to an extent of $\geq 95\%$ by weight, or to an extent of $\geq 96\%$ by weight, or to an extent of $\geq 97\%$ by weight, or to an extent of $\geq 98\%$ by weight, or to an extent of $\geq 99\%$ by weight (in each case the weight of the liquid phase P).

The content in a liquid phase P to be treated in accordance with the invention (or in another liquid phase) of glyoxal (i.e. the total content in the liquid phase P of monomeric glyoxal, monomeric glyoxal monohydrate and monomeric glyoxal dihydrate) is determined in this document as follows:

First, a derivatization solution D is prepared. To this end, 2.0 g of a 50% by weight solution of 2,4-dinitrophenylhydrazine (manufacturer: Aldrich, purity: $\geq 97\%$) is dissolved at a temperature of 25° C. in 62 ml of 37.0% by weight aqueous hydrochloric acid (manufacturer: Aldrich, purity: $\geq 99.999\%$). The resulting solution is subsequently (likewise at a temperature of 25° C.) stirred into 335 g of distilled water. After stirring at 25° C. for 1 hour, the derivatization solution D is obtained by filtration as the resulting filtrate.

To determine the content in a liquid phase P of glyoxal, 1 g (this amount can be increased correspondingly if required) of the derivatization solution D is weighed into a screwtop tube whose capacity is 10 ml. Subsequently, a sample of the liquid phase P is weighed into the screwtop tube thus filled, the amount of which is in the range from 0.15 to 2.0 g.

The entire contents of the screwtop tube are then mixed by shaking and then left to stand at a temperature of 25° C. over a period of 10 minutes. During this time, the corresponding hydrazone H of monomeric glyoxal forms from the monomeric glyoxal present in the screwtop tube by chemical reaction with 2,4-dinitrophenylhydrazine. During this time, the 2,4-dinitrophenylhydrazine, however, also removes the monomeric glyoxal present in bound form in the monomeric glyoxal monohydrate and glyoxal dihydrate present in the screwtop tube therefrom in the form of the hydrazone H (a corresponding removal of monomeric glyoxal from polyglyoxal hydrates present in the screwtop tube, in contrast, essentially does not take place).

Addition of 0.5 g of glacial acetic acid (manufacturer: Aldrich, purity: $\geq 99.8\%$) to the screwtop tube subsequently freezes the hydrazone formation which has occurred. When the addition of acetic acid is accompanied by formation of solid precipitate, further acetic acid is added gradually in order to redissolve the precipitate formed (but the total amount of acetic acid added must not exceed 1.0 g). When the precipitate formed still has not gone into solution even on attainment of the limit (1.0 g) in the total amount of acetic acid addition allowed, 0.5 g of dimethyl phthalate is weighed in. If this too is incapable of dissolving the precipitate formed, the amount of dimethyl phthalate added is increased gradually in order to bring about this dissolution (but the total amount of dimethyl phthalate added must not exceed 1.0 g). When the precipitate formed still has not gone into solution even on attainment of the limit (1.0 g) in the total amount of dimethyl phthalate addition allowed, 2 g of a mixture G of 9 g of acetonitrile and 1 g of dimethyl phthalate are added. If this addition too is incapable of dissolving the precipitate, the amount of mixture G added is increased gradually in order to bring about this dissolution. Normally, the total amount of mixture G added in order to bring about the dissolution of the precipitate does not exceed 5 g (all above dissolution tests are carried out at 25° C.).

The solution of the hydrazone H obtained in the screwtop tube as described is subsequently analyzed for its hydrazone content by means of HPLC (High Pressure Liquid Chromatography) using the following operating conditions (the molar amount thereof results directly in the molar amount of glyoxal present in the liquid phase P):

Chromatography column to be used: Waters Symmetry C18, 150×4.6 mm, 5 µm (from Waters Associates, Milford, Mass., USA);

Injection volume of the solution to be analyzed: 50 µl (time t=0);
Temperature: 40° C.;
Eluent flow rate: 1.5 ml/min;
Analysis time: 17 min;
Equilibration time: 8 min;
Eluent: in the period t from >0 min to 15 min, a mixture of 30% by weight of acetonitrile, 50% by weight of water and 20% by weight of tetrahydrofuran (each HPLC grade);
in the period from >15 min to 17 min, a mixture of 65% by weight of acetonitrile, 30% by weight of water and 5% by weight of tetrahydrofuran;
in the period from >17 min to 25 min, a mixture of 30% by weight of acetonitrile, 50% by weight of water and 20% by weight of tetrahydrofuran (then the column is equilibrated and ready for use again for the next analysis).

The retention time of the glyoxal as the hydrazone H is 7.613 min under the above conditions.

The analysis is effected by means of monochromatic radiation of wavelength 365 nm.

The analysis method employed is absorption spectroscopy.

The variation of the eluent over the elution time ensures an increased separating action (in general, the liquid phase P, as well as glyoxal, also comprises other by-product aldehydes and/or by-product ketones which form the particular corresponding hydrazone with 2,4-dinitrophenylhydrazine).

To calibrate the HPLC method, appropriately in application terms, a solution of monomeric glyoxal in methanol will be used, which comprises 50 ppm by weight of monomeric glyoxal.

For this purpose, it is treated by means of the derivatization solution D as described above and then subjected to the HPLC analysis described.

One notable feature of the process according to the invention is, as already stated, that it is not reliant on the use of high-purity $C_3$ precursor compounds of acrylic acid for the heterogeneously catalyzed partial gas phase oxidation to prepare acrylic acid.

For example, for the heterogeneously catalyzed partial gas phase oxidation to prepare acrylic acid, it is possible to use a starting reaction gas mixture which, based on the molar amount of the $C_3$ precursor compound (e.g. propane, propylene, acrolein, propionic acid, propionaldehyde, propanol and/or glycerol) present therein, contains a molar total amount of $C_2$ compounds (e.g. ethane, ethylene, acetylene, acetaldehyde, acetic acid and/or ethanol) of ≧200 molar ppm, or ≧250 molar ppm, or ≧300 molar ppm, or ≧400 molar ppm, or ≧500 molar ppm, or ≧750 molar ppm, or ≧1000 molar ppm, or ≧1250 molar ppm, or ≧1500 molar ppm.

The starting reaction gas mixture is that gas mixture which is supplied to the catalyst bed for the purpose of partial oxidation of the $C_3$ precursor compound present therein to acrylic acid. As well as the $C_3$ precursor compound, undesired impurities and molecular oxygen as the oxidizing agent, the starting reaction gas mixture generally also comprises inert diluent gases, for example $N_2$, $CO_2$, $H_2O$, noble gas, molecular hydrogen, etc. Any inert diluent gas is normally such that it remains unchanged to an extent of at least 95 mol % of its starting amount in the course of the heterogeneously catalyzed partial oxidation.

The proportion of the $C_3$ precursor compound in the starting reaction gas mixture may, for example, be in the range from 4 to 20% by volume, or from 5 to 15% by volume, or from 6 to 12% by volume.

Normally, the starting reaction gas mixture comprises, based on the stoichiometry of the partial oxidation reaction of the $C_3$ precursor compounds to acrylic acid, an excess of molecular oxygen, in order to reoxidize the generally oxidic catalysts again.

In the case of subsequent application of the inventive procedure, this excess can be selected at a particularly high level, since an increasing oxygen excess is generally also accompanied by an increase in undesired secondary component formation of glyoxal.

In the same way, in the heterogeneously catalyzed partial gas phase oxidation of the $C_3$ precursor compounds to acrylic acid, the maximum reaction temperature present in the catalyst bed can be selected at a comparatively elevated level when the process according to the invention is employed after the partial oxidation. One reason for this is that an increasing maximum temperature is generally also accompanied by an increase in the undesired secondary component formation of glyoxal. However, the employment of elevated maximum temperatures generally permits the use of catalysts with lower activity, which opens up the possibility of prolonged catalyst service life. However, in the case of use of catalysts with lower activity with increasing conversion of the $C_3$ precursor compound, undesired full combustion thereof frequently also proceeds to an increasing degree. A by-product formed may in some cases likewise be glyoxal.

In the context of the inventive procedure, it is similarly also possible to proceed in a more generous manner in the selection of the loading of the catalyst bed with $C_3$ precursor compound.

In addition, it has been found that the glyoxal by-product formation is promoted by elevated water vapor contents in the reaction gas mixture. The process according to the invention is therefore of relevance not least when the starting reaction gas mixture used for the heterogeneously catalyzed partial gas phase oxidation of the $C_3$ precursor compound comprises ≧1% by weight, or ≧2% by weight, or ≧3% by weight, or ≧4% by weight, or ≧5% by weight, or ≧7% by weight, or ≧9% by weight, or ≧15% by weight, or ≧20% by weight of water vapor. In general, the water vapor content of the starting reaction gas mixture will, however, not be more than 40% by weight, frequently not more than 30% by weight.

Otherwise, the process for heterogeneously catalyzed partial gas phase oxidation for preparing acrylic acid can be carried out in a manner known per se as described in the prior art.

When the $C_3$ precursor compound is, for example, propylene and/or acrolein, the heterogeneously catalyzed partial gas phase oxidation can be carried out, for example, as described in documents WO 2005/042459, WO 2005/047224 and WO 2005/047226.

When the $C_3$ precursor compound is, for example, propane, the heterogeneously catalyzed partial gas phase oxidation for preparing acrylic acid can be carried out, for example, as described in documents EP-A 608 838, DE-A 198 35 247, DE-A 102 45 585 and DE-A 102 46 119.

When the $C_3$ precursor compound is, for example, glycerol, the heterogeneously catalyzed partial gas phase oxidation for preparing acrylic acid can be carried out, for example, as described in documents WO 2007/090991, WO 2006/114506, WO 2005/073160, WO 2006/114506, WO 2006/092272 or WO 2005/073160.

It has also already been proposed to obtain the propylene as the $C_3$ precursor compound by a partial dehydrogenation and/or oxydehydrogenation of propane preceding the partial gas phase oxidation (e.g. WO 076370, WO 01/96271, EP-A 117146, WO 03/011804 and WO 01/96270).

To remove the acrylic acid from the product gas mixture of the heterogeneously catalyzed partial gas phase oxidation of a C₃ precursor compound, a combination of different separation processes is normally employed in principle, in order to achieve a purity of the acrylic acid appropriate for the subsequent end use thereof in a very economically viable manner. The combination employed in the individual case depends not least on the type and amount of the constituents other than acrylic acid which are present in the product gas mixture. A liquid phase P treatable in accordance with the invention can therefore be obtained in a wide variety of different ways.

An essential constituent of such a combination of separation processes is normally noncrystallizative thermal separation processes. The noncrystallizative thermal separation processes are those separation processes in which gaseous (ascending) and liquid (descending) streams or two liquid streams are conducted in countercurrent within separating columns comprising separating internals, the gradients which exist between the streams giving rise to heat and mass transfer, which ultimately causes the separation desired in the separating column.

Examples of such noncrystallizative thermal separation processes are (partial) condensation, fractional condensation (cf. DE-A 199 24 532) and rectification.

The resulting separating action is based here in particular on the difference of the boiling points of acrylic acid and the secondary components other than acrylic acid. A further example is that of absorption. The separating action is based here especially on the different solubility of acrylic acid and the secondary components other than acrylic acid in the absorption liquid. The above also applies to the noncrystallizative thermal separation processes of stripping (a stripping gas takes up constituents dissolved in a liquid therefrom with different affinity) and desorption (the reverse process of absorption; material dissolved in the liquid phase is removed by lowering the partial pressure). The term "thermal separation processes", however, also comprises azeotropic distillation and rectification (they exploit the different degree to which acrylic acid and the secondary components (the constituents other than acrylic acid in the reaction gas mixture of the partial oxidation) tend to form azeotropes with added azeotroping agents). In addition, the term "noncrystallizative thermal separation processes" comprises extraction.

A feature common to essentially all possible combinations of thermal separation processes for removing acrylic acid from the product gas mixture of the heterogeneously catalyzed partial gas phase oxidation of a C₃ precursor compound is that, if appropriate after direct and/or indirect cooling of the aforementioned product gas mixture, acrylic acid present in the product gas mixture is converted in a basic removal step to the condensed (especially liquid) phase (appropriately for application purposes, at least a portion of residual gas remaining in gaseous form in such as basic removal is recycled as "cycle gas" into the partial heterogeneously catalyzed gas phase oxidation of the C₃ precursor compound (for example into the starting reaction gas mixture thereof) ("cycle gas method"); in general, residual gas (cycle gas) consists predominantly of the inert diluent gases additionally used for the partial heterogeneously catalyzed gas phase oxidation of the C₃ precursor compound and of water vapor typically formed as a by-product in the partial oxidation, and by-products (e.g. carbon oxides) formed by the route of undesired full oxidation of the C₃ precursor compound, which may also comprise glyoxal; when the basic removal is an absorption, the cycle gas may also comprise absorbents; in some cases it still comprises small amounts of molecular oxygen (residual oxygen) unconsumed in the partial oxidation and/or of unconverted organic C₃ precursor compound (cf., for example, WO 2004/007405 and DE-A 102007019597)).

This can be done, for example, by absorption into a suitable solvent (for example water, high-boiling organic solvents, aqueous solutions) and/or by means of partial or essentially full condensation (e.g. fractional condensation) (on this subject, cf., for example, documents EP-A 13 88 533, EP-A 13 88 532, DE-A 102 35 847, EP-A 79 28 67, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 85 41 29, US-A 4,317,926, DE-A 198 37 520, DE-A 196 06 877, DE-A 190 50 1325, DE-A 102 47 240, DE-A 197 40 253, EP-A 69 57 36, EP-A 98 22 87, EP-A 10 41 062, EP-A 11 71 46, DE-A 43 08 087, DE-A 43 35 172, DE-A 44 36 243, DE-A 19 924 532, DE-A 103 32 758 and DE-A 19 924 533). An acrylic acid removal can also be undertaken as in EP-A 98 22 87, EP-A 98 22 89, DE-A 103 36 386, DE-A 101 15 277, DE-A 196 06 877, DE-A 197 40 252, DE-A 196 27 847, EP-A 92 04 08, EP-A 10 68 174, EP-A 10 66 239, EP-A 10 66 240, WO 00/53560, WO 00/53561, DE-A 100 53 086 and EP-A 98 22 88. Favorable methods of removal are also the processes described in documents WO 2004/063138, WO 2004/035514, DE-A 102 43 625 and DE-A 102 35 847.

The further separation steps to be employed in order to remove the acrylic acid in the desired purity from the liquid (or generally condensed) phase comprising the acrylic acid target product in the basic removal described may, according to the objective, be a wide variety of different combinations of adsorptive, extractive, desorptive, distillative, stripping, rectificative, azeotropically distillative, azeotropically rectificative and crystallizative processes.

When a liquid phase P is passed through, or the liquid phase which comprises the acrylic acid target product and is obtained in the course of the basic removal described is already a liquid phase P, the process according to the invention for removing glyoxal present in the liquid phase P can advantageously be employed. The fact that, in the case of application of the inventive procedure to a liquid phase P (i.e. in the case of cooling of a liquid phase P), acrylic acid regularly crystallizes out is caused by the high minimum content of acrylic acid required therein. This may, as already stated, for example, be from $\geq 70$ to $\leq 99.5\%$ by weight, or from $\geq 80$ to $\leq 99.5\%$ by weight, or from $\geq 85$ to $\leq 99\%$ by weight, or from $\geq 90$ to $\leq 98\%$ by weight, or from $\geq 93$ to $\leq 97\%$ by weight.

In this case, the crystallization process according to the invention can be executed in the same way and be integrated in the same way into the overall process for removing (glacial) acrylic acid from the product gas mixture of the heterogeneously catalyzed partial gas phase oxidation of the C₃ precursor compound, as taught especially by the following prior art documents: WO 02/055469, WO 03/078378, WO 01/77056, WO 03/041833, DE-A 196 06 877, DE-A 103 36 386, WO 98/01414, WO 01/77056, EP-A 1 484 308, EP-A 1 484 309, US-A 2004/0242826, DE-A 102 43 625, DE-A 196 06 877, EP-A 792 867, EP-A 1 015 410, EP-A 920 408, EP-A1 189 861, EP-A1 015 411, EP-A1 068 174, WO 2004/035514, EP-A 1 066 293, EP-A1 163 201, EP-A1 159 249, WO 02/090310, DE-A 101 22 787, WO 03/041832, DE-A 102 35 847, EP-A 1 252 129, EP-A 616 998, EP-A 1 388 533, EP-A1 125 912 and EP-A1 116 709.

The process according to the invention is of very particular significance when the liquid phase P which comprises acrylic acid as a main constituent and glyoxal as a by-product and is to be treated in accordance with the invention is obtained from the product gas mixture of a heterogeneously catalyzed partial gas phase oxidation of at least one C₃ precursor of acrylic acid employing at least one noncrystallizative thermal separation process. This is especially true when mother liquor which remains in the inventive crystallizative removal of the glyoxal present in the liquid phase P (said mother liquor then comprising the glyoxal in enriched form) is recycled into at least one of the noncrystallizative thermal separation processes employed to prepare the liquid phase P.

The base structure of such a combined application of noncrystallizative thermal separation processes and crystallizative separation processes is taught, for example, by DE-A 196 06 877, EP-A 792 867 and EP-A 1 484 308, EP-A 1 484 309, EP-A 1 116 709 and especially EP-A 1 015 410.

The process according to the invention is of increased significance in the case of such a combination in that, in the case of continuous operation of such a procedure, the glyoxal accumulates in the liquid phase P to be treated in accordance with the invention as a result of the mother liquor recycling, since the mother liquor (as already mentioned) comprises the glyoxal in enriched form. In other words, even comparatively small glyoxal contents in the product gas mixture of the gas phase oxidation can thus grow to become a serious problem (a liquid phase P to be treated in accordance with the invention (which then comprises at least 200 molar ppm of glyoxal based on the molar amount of acrylic acid present therein) can actually arise at all under some circumstances in the course of the continuous operating time from an initially nonliquid phase P (which initially comprises less than 200 molar ppm of glyoxal based on the molar amount of acrylic acid present therein)). An above-average depletion coefficient $A^{Gly}$ is indispensible in these cases for a successful process performance.

The elevated glyoxal content required in accordance with the invention in liquid phases P may, however, also be present therein, for example, when mother liquors obtained in the crystallization of liquid phases which comprise acrylic acid and have only relatively low glyoxal contents are crystallized further for the purpose of enhancing the yield, or when secondary streams which may be contaminated in the inventive manner and are obtained in noncrystallizative thermal separation processes on the route to preparation of pure acrylic acid are treated in accordance with the invention for the purpose of enhancing the yield.

Since water is normally inevitably formed as a by-product and may additionally be used as an inert diluent gas in the reaction gas mixture in the heterogeneously catalyzed partial gas phase oxidation of $C_3$ precursor compounds, the liquid phase P to be treated in accordance with the invention frequently comprises not only water but, as well as monomeric glyoxal, simultaneously also both monomeric glyoxal monohydrate and monomeric glyoxal dihydrate. In some cases, however, only monomeric glyoxal may be present in a liquid phase P to be treated in accordance with the invention (one advantage of the inventive procedure is that it is effective in both cases).

In other words, the process according to the invention can especially also be employed when the glyoxal present in the liquid phase P is present in the liquid phase P in the form of monomeric glyoxal monohydrate and/or monomeric glyoxal dihydrate to an extent of at least 30 mol %, or to an extent of at least 50 mol %, or to an extent of at least 70 mol %, or to an extent of at least 90 mol %, or to an extent of at least 95 mol %.

Frequently, the liquid phase P, based on the amount of acrylic acid present therein, comprises from 0.20 to 30%, or from 0.20 to 20%, or from 0.20 to 10% by weight of water (the hydrate water (of, for example, glyoxal hydrates) is included in this amount of water). In many cases, the aforementioned water content of the liquid phase P, based on the amount of acrylic acid present therein, is from 0.50 to 30% by weight, or from 0.50 to 20% by weight, or from 0.50 to 10% by weight.

The at least one noncrystallizative thermal separation process employed to obtain the liquid phase P to be treated in accordance with the invention from the product gas mixture of a heterogeneously catalyzed partial gas phase oxidation of a $C_3$ precursor of acrylic acid (into which mother liquor (which then comprises the glyoxal in enriched form) which remains in the course of the subsequent inventive crystallizative removal of the glyoxal present in the liquid phase P may be at least partly recycled) will generally be a rectification, azeotropic rectification, absorption, adsorption, extraction, desorption, destraction, partial condensation, stripping, fractional condensation or a combination of a plurality of these processes. Frequently, the liquid phase P to be treated in accordance with the invention will be obtained by employing the aforementioned processes more than once.

In the simplest case, the liquid phase P to be treated in accordance with the invention may be the absorbate and/or partial condensate and/or condensate obtained by fractionation from an absorptive and/or condensative removal of acrylic acid from the product gas mixture of a heterogeneously catalyzed partial gas phase oxidation of at least one of the $C_3$ precursors listed in this document. According to the invention, the mother liquor comprising enriched glyoxal is then recycled into the absorption and/or (optionally fractional) condensation. Appropriately, a networked mode of operation to be employed as described, composed of at least one noncrystallizative thermal separation process to obtain the liquid phase P to be treated in accordance with the invention and the inventive crystallizative glyoxal removal from the liquid phase P thus obtained, in which mother liquor which comprises enriched glyoxal and is obtained in the crystallizative glyoxal removal is recycled at least partly into at least one of the noncrystallizative thermal separation processes employed to obtain the liquid phase P to be treated in accordance with the invention, has an outlet for at least one stream comprising enriched glyoxal.

Advantageously, this outlet is on the side of the noncrystallizative thermal separation processes. In general, the bottoms liquid of a separation column will be used as such an outlet, from which the liquid phase P to be treated in accordance with the invention itself or the stream to be converted later to the liquid phase P to be treated in accordance with the invention is withdrawn, for example, via side withdrawal (generally, such an outlet should be below the aforementioned side withdrawal). When the liquid phase P to be treated in accordance with the invention is, for example, a condensate fraction obtained via side withdrawal from the product gas mixture of the heterogeneously catalyzed partial gas phase oxidation of the $C_3$ precursor compound as described in documents PCT/EP2008/050785, DE-A 102007055086 and EP-A 1 554 234, the outlet from the redissociation apparatus (the cleavage apparatus) for the Michael adduct acrylic acid oligomers may also function as the glyoxal outlet addressed above. In this case, it becomes noticeable in an advantageous manner that glyoxal is converted at elevated temperature (in the absence of particular redissociation catalysts) primarily to the polyglyoxals mentioned or hydrates thereof.

In general, when the liquid phase P to be treated in accordance with the invention is withdrawn from a separation column, for example via side withdrawal, in which a noncrystallizative thermal separation process is carried out in the presence of an aqueous absorbent conducted from the top downward in the separation column and/or of an aqueous reflux liquid, the further down the withdrawal point is in the separation column, the greater the glyoxal content in the withdrawn liquid phase P will be.

However, a glyoxal outlet may also or only be present on the side of the inventive removal, i.e. on the crystallizative side. In this case, the outlet will normally consist of mother liquor comprising enriched glyoxal.

When the inventive removal is performed, for example, by means of a combination of dynamic and static crystallization according to EP-A 616 998, the glyoxal outlet comprising enriched glyoxal will generally (appropriately from an application point of view) be in the region of the static crystallization.

The latter is the case especially when, in the case of employment of the process according to the invention, no recycling of mother liquor comprising enriched glyoxal into at least one noncrystallizative thermal separation process is carried out.

The process according to the invention is favorable not least when the liquid phase P to be treated in accordance with the invention (for example by means of one of the procedures described above) derives from a product gas mixture of a heterogeneously catalyzed partial gas phase oxidation of a $C_3$ precursor of acrylic acid, which, based on the molar amount of acrylic acid present in the product gas mixture, comprises at least 200 molar ppm of glyoxal, or $\geq 250$ molar ppm of glyoxal, or $\geq 300$ molar ppm of glyoxal, or $\geq 400$ molar ppm of glyoxal, or $\geq 500$ molar ppm of glyoxal, or $\geq 750$ molar ppm of glyoxal, or $\geq 1000$ molar ppm of glyoxal, or $\geq 1250$ molar ppm of glyoxal, or $\geq 1500$ molar ppm of glyoxal.

Normally, the aforementioned glyoxal contents of the product gas mixture (on the same basis) will be $\leq 5$ mol %. In many cases, the acrylic acid content of the aforementioned product gas mixtures will be from 1 to 30% by volume.

The process according to the invention can also be employed especially when the liquid phase P to be treated in accordance with the invention is obtained by subjecting the product gas mixture which may have been cooled beforehand by direct and/or indirect heat exchange to an absorption of the acrylic acid out of the product gas mixture with an aqueous solution or with water (cf., for example, EP-A 1 388 532 and EP-A 1 388 533). The resulting aqueous absorbate comprising the acrylic acid may directly be the liquid phase P to be treated in accordance with the invention.

Should the acrylic acid content of the aqueous absorbate, however, still be below 70% by weight (based on the weight of the absorbate)—or else for other reasons—the aqueous absorbate (if appropriate after a preceding desorption and/or stripping of constituents having a lower boiling point than acrylic acid in the absorbate) can be subjected to an azeotropic distillation (rectification) to remove at least a portion of the water present in the absorbate, and then the remaining residue (as the liquid phase P) can be subjected to the inventive crystallizative removal. Azeotroping agents suitable in this context include, for example, heptane, dimethylcyclohexane, ethylcyclohexane, toluene, ethylbenzene, octane, chlorobenzene, xylene or mixtures (for example of 60% by weight of toluene and 40% by weight of heptane).

The alternative azeotroping agents used may, however, also be methyl isobutyl ketone or isopropyl acetate.

Further suitable azeotroping agents are disclosed by US 2004/0242826, EP-A 778 255, EP-A 695 736 and the prior art cited in these documents. Typically, the azeotropic distillation or rectification is advantageously carried out at working pressures below atmospheric pressure.

The present application thus comprises, more particularly, a process according to the invention in which the acrylic acid and glyoxal, together with other constituents having lower and higher boiling points than acrylic acid, are transferred from the product gas mixture of the heterogeneously catalyzed partial gas phase oxidation to an aqueous liquid phase (for example by absorption by means of an aqueous solution), and at least a portion of the water is removed from the resulting aqueous liquid phase by means of azeotropic rectification and/or distillation to leave a liquid phase P which is subsequently treated by crystallization in accordance with the invention.

In principle, it is possible to proceed as described in documents EP-A 1 298 120 and EP-A 1 396 484, but there is no longer any need to take the particular measures required in these documents.

At this point, it should be emphasized that, in a fractional condensation of the product gas mixture, it is, appropriately in application terms (if appropriate after preceding direct and/or indirect cooling of the product gas mixture (for example with a quench fluid according to EP-A 1 066 239, or according to EP-A 1 163 201)), fractionally condensed in a separation column having separating internals ascending into itself with side draw removal of crude acrylic acid (which, if appropriate, forms the liquid phase P to be treated in accordance with the invention; if appropriate, the crude acrylic acid is also treated by rectification and/or distillation to obtain the liquid phase P) (cf. also EP-A 1 015 410, WO 2004/035514, DE-A 102 43 625, EP-A 1 015 411, DE-A 102 35 847, EP-A 1 159 249, EP-A 1 163 201, EP-A 1 066 239 and EP-A 920 408). In order to minimize any acrylic acid losses which occur in the course of fractional condensation, an absorption with water and/or aqueous solution may, if appropriate, additionally be superimposed on the fractional condensation.

A liquid phase obtained in this way by condensation (and if appropriate additional rectification) will then appropriately be subjected to an inventive crystallizative removal when it has both the acrylic acid content required in this regard and the relevant content of glyoxal based on the acrylic acid content.

This mother liquor which comprises enriched glyoxal which is formed can then, as already mentioned at various points in this document, for example according to the example of EP-A 920 408, or WO 2004/035514, or EP-A 1 554 234, or the application PCT/EP2008/050785 or DE-A 102007055086, be recycled at least partly, preferably fully, into the fractional condensation of acrylic acid out of the product gas mixture.

In that case, the glyoxal outlet will be sited below the side draw of the crude acrylic acid.

The inventive crystallizative treatment of the liquid phase P, especially of a liquid phase P obtained by condensation and/or absorption and/or rectification in the aforementioned manner, is in principle not subject to any restriction, including the processes for removing the mother liquor from the crystals (all processes detailed in the prior art cited in this document can be employed).

In other words, it can be carried out in one stage, or more than one stage, continuously or batchwise. In particular, it can also be carried out as a fractional crystallization. Typically, in a fractional crystallization, all stages which produce acrylic acid crystals which are purer (especially in terms of glyoxal) than the liquid phase P supplied are referred to as purification stages, and all other stages as stripping stages. Appropriately, multistage processes are operated by the countercurrent principle, in which the crystals are removed from the mother liquor after the crystallization in each stage and these crystals are supplied to the particular stage with the next highest purity, while the crystallization residue is supplied to the particular stage with the next lowest purity.

In general, the temperature of the liquid phase P during the process according to the invention is between −25° C. and +14° C., especially between +12° C. and −5° C.

For example, the process according to the invention can be performed as a layer crystallization (cf. DE-A 2606364, EP-A 616998, EP-A 648520 and EP-A 776875). In this case, the crystals are frozen out in the form of coherent, firmly adhering layers. The crystals deposited are separated from the remaining residual melt (the mother liquor) by virtue of the residual melt simply flowing off. In principle, a distinction is drawn between "static" and "dynamic" layer crystallization processes. A characteristic feature of dynamic layer crystallization of the liquid phases P is the forced convection of the liquid phase P. This can be effected by pumped circulation of the liquid phase P through tubes with full flow, by application of the liquid phase P as a trickle film (for example according to EP-A 616998) or by introducing inert gas into a liquid phase P or by pulsation.

In the static processes, the liquid phase P is at rest (for example in tube bundle or plate heat exchangers) and separates out in the form of layers on the secondary side by virtue of slow lowering of the temperature. Thereafter, the residual melt (mother liquor) is discharged, relatively highly contaminated fractions are sweated out of the crystal layer by slowly increasing the temperature and then the pure product is melted off (cf. WO 01/77056).

Preferably in accordance with the invention, the process according to the invention in the case of all liquid phases P described in this document will, however, be performed as a suspension crystallization according to the teaching of WO 01/77056, of WO 02/055469, of EP-A 1 554 234, of PCT/EP2008/050785, of DE-A 102007055086, of German application 102007043759.7, of German application 102007043758.9, of German application 102007043748.1 and of WO 03/078378.

In general, a crystal suspension comprising suspended acrylic acid crystals is obtained by cooling the liquid phase P, these acrylic acid crystals having a lower glyoxal content and the remaining residual melt (mother liquor) a higher glyoxal content (relative based on the particular total amount) than the liquid phase P to be purified. These acrylic acid crystals may grow immediately in suspension and/or be deposited as a layer on a cooled wall, from which they are subsequently scraped off and resuspended in the residual melt (mother liquor).

All suspension crystallizers and suspension crystallization processes detailed in WO 01/77056, WO 02/055469, EP-A 1 554 234, PCT/EP2008/050785, DE-A 102007055086, German application 102007043759.7, German application 102007043758.9, German application 102007043748.1 and WO 03/078378 are possibilities in accordance with the invention. In general, the acrylic acid crystal suspension obtained has a solids content of from 20 to 40% by weight.

In addition, all processes mentioned in the aforementioned publications (especially in the aforementioned WO publications) for separating suspension crystals formed and mother liquor remaining are useful (for example mechanical separation processes such as centrifugation). Preferably in accordance with the invention, the separation is effected in a wash column. This is preferably a wash column with forced transport of the acrylic acid crystals deposited. The proportion by volume of crystals in the crystal bed generally reaches values of >0.5. In general, the wash column is operated at values of from 0.6 to 0.75. The wash liquid used is advantageously the melt of acrylic acid crystals which have been purified (removed) beforehand in the wash column. The washing is normally effected in countercurrent. The process according to the invention thus comprises especially processes which comprise the following process steps:

a) crystallizing acrylic acid out of a liquid phase P,
b) separating the acrylic acid crystals from the remaining mother liquor (residual melt, liquid residual phase),
c) at least partially melting the acrylic acid crystals removed and
d) at least partly recycling the molten acrylic acid crystals to step b) and/or to step a).

Preference is given to effecting step b) by countercurrent washing with molten acrylic acid crystals which have been removed beforehand and recycled into step b).

Especially when the crystallization is performed as a suspension crystallization, and even more especially when the subsequent mother liquor removal is performed in a wash column, and even more especially when the wash liquid used is the melt of acrylic acid crystals which have already been purified beforehand in the wash column, it is found to be favorable that the liquid phase P frequently comprises water.

In other words, the process according to the invention comprises not least processes in which the liquid phase P to be purified is converted under cold conditions to a crystal suspension consisting of acrylic acid crystals and liquid residual phase (residual melt), the proportion by weight of glyoxal in the acrylic acid crystals being less and the proportion by weight of glyoxal in the liquid residual phase (the mother liquor) being greater than the proportion by weight of glyoxal in the liquid phase P, a portion of the remaining mother liquor is, if appropriate, removed mechanically from the crystal suspension and the acrylic acid crystals are freed of remaining mother liquor in a wash column (cf., for example, WO 01/77056, WO 03/041832, WO 03/041833 and WO 98/01414), with the proviso that a) the liquid phase P, based on the acrylic acid present therein, comprises from 0.20 to 30%, frequently to 20%, often to 10% by weight of water, and
b) the wash liquid used is the melt of acrylic acid crystals purified in the wash column.

In particular, the process according to the invention comprises the above processes wherein the liquid phase P contains $\geqq 80\%$ by weight of acrylic acid, or $\geqq 90\%$ by weight of acrylic acid, or $\geqq 95\%$ by weight of acrylic acid.

In addition, it is advantageous in accordance with the invention when the water content of the liquid phase P in above-described procedures (or quite generally when the process according to the invention is employed), based on acrylic acid present in the liquid phase P, is from 0.2 or 0.4 to 8%, or to 10%, or to 20%, or to 30% by weight, or from 0.6 to 5% by weight, or from 0.6 to 3% by weight.

Of course, the process according to the invention can also be applied to all crude acrylic acids mentioned in the documents cited as prior art in this document, provided that they comprise the required acrylic acid content and additionally the required glyoxal content.

All of the above applies in particular when the wash column is a wash column with forced transport of the acrylic acid crystals, and in particular when it is a hydraulic or a mechanical wash column, for example according to WO 01/77056, and it is operated as detailed there.

All of the above is true in particular when the wash column is designed and operated according to the teachings of WO 03/041832 and of WO 03/041833.

The process according to the invention thus permits, with the sequence of partial oxidation of at least one $C_3$ precursor to obtain a product gas mixture having an elevated glyoxal content, fractional acrylic acid condensation from the product gas mixture of the partial oxidation, suspension crystallization of the acrylic acid condensate withdrawn and removal of the suspension crystals from remaining mother liquor in a wash column using a pure crystal melt as the wash liquid, in a highly efficient manner and employing only one crystallization stage, the preparation of acrylic acid which can be referred to as free of glyoxal and is thus superabsorbent-grade (such acrylic acid can of course also be used for all other uses addressed in WO 02/055469 and WO 03/078378, in particular when the starting material is a cheap $C_3$ precursor raw material source for the partial oxidation which causes the formation of glyoxal by-product).

It will be appreciated that all process steps detailed in this document are performed with inhibition of polymerization. It is possible to proceed as described in the prior art cited. An outstanding position among the entirety of the available acrylic acid process stabilizers is assumed by dibenzo-1,4-thiazine (PTZ), 4-hydroxy-2,2,6,6-tetramethylpiperidine 1-oxyl (4-OH-TEMPO) and p-methoxyphenol (MEHQ), each of which may alone or in pairs or as a three-substance mixture be part of the liquid phase P to be treated in accordance with the invention. Typically, the total amount of polymerization inhibitors present in the liquid phase P, based on the total amount of acrylic acid present therein, is from 0.001 to 2% by weight.

Owing to undesired formation of acrylic acid oligomers (Michael adducts) in the liquid phase P, when it is left to stand, the process according to the invention is employed as immediately as possible after obtaining the liquid phase P.

In a manner advantageous in accordance with the invention, when the process according to the invention is employed, for example, $C_4$ partial oxidation conversion products (e.g. butene-1, butadiene, n-butane, etc.) present in the liquid phase P, for example methacrylic acid, butyric acids, butyraldehydes, etc., are also removed. They may, based on the molar amount of acrylic acid present, be present in the same amounts as glyoxal in the liquid phase P (more particularly in all liquid phases P cited explicitly in this document). The same applies to acrolein, formaldehyde, acetaldehyde, propionaldehyde and all $C_5$ and $C_6$ partial oxidation conversion products, and any polyglyoxals and polyglyoxal hydrates present in the liquid phase P.

The present invention thus comprises especially the following embodiments:

1. A process for separating acrylic acid present as a main product and glyoxal present as a by-product in a product gas mixture of a partial heterogeneously catalyzed gas phase oxidation of a $C_3$ precursor compound of acrylic acid, in which a liquid phase P is obtained which consists of acrylic acid to an extent of at least 70% of its weight and, based on the molar amount of acrylic acid present therein, comprises at least 200 molar ppm of glyoxal, which comprises separating the glyoxal from the acrylic acid in the liquid phase P by crystallization, the acrylic acid being enriched in the crystals formed and the glyoxal in the mother liquor which remains in the course of crystallization.
2. The process according to embodiment 1, wherein the liquid phase P, based on the molar amount of acrylic acid present therein, comprises at least 300 molar ppm of glyoxal.
3. The process according to embodiment 1, wherein the liquid phase P, based on the molar amount of acrylic acid present therein, comprises at least 400 molar ppm of glyoxal.
4. The process according to embodiment 1, wherein the liquid phase P, based on the molar amount of acrylic acid present therein, comprises at least 500 molar ppm of glyoxal.
5. The process according to embodiment 1, wherein the liquid phase P, based on the molar amount of acrylic acid present therein, comprises at least 1000 molar ppm of glyoxal.
6. The process according to embodiment 1, wherein the liquid phase P, based on the molar amount of acrylic acid present therein, comprises at least 1500 molar ppm of glyoxal.
7. The process according to any one of embodiments 1 to 6, wherein the liquid phase P consists of acrylic acid to an extent of at least 75% of its weight.
8. The process according to any one of embodiments 1 to 6, wherein the liquid phase P consists of acrylic acid to an extent of at least 80% of its weight.
9. The process according to any one of embodiments 1 to 6, wherein the liquid phase P consists of acrylic acid to an extent of at least 85% of its weight.
10. The process according to any one of embodiments 1 to 6, wherein the liquid phase P consists of acrylic acid to an extent of at least 90% of its weight.
11. The process according to any one of embodiments 1 to 6, wherein the liquid phase P consists of acrylic acid to an extent of at least 95% of its weight.
12. The process according to any one of embodiments 1 to 6, wherein the liquid phase P consists of acrylic acid to an extent of at least 96% of its weight.
13. The process according to any one of embodiments 1 to 6, wherein the liquid phase P consists of acrylic acid to an extent of at least 97% of its weight.
14. The process according to any one of embodiments 1 to 13, wherein the $C_3$ precursor compound is propylene.
15. The process according to any one of embodiments 1 to 13, wherein the $C_3$ precursor compound is acrolein.
16. The process according to any one of embodiments 1 to 13, wherein the $C_3$ precursor compound is propane.
17. The process according to any one of embodiments 1 to 13, wherein the $C_3$ precursor compound is glycerol.
18. The process according to any one of embodiments 1 to 17, wherein a starting reaction gas mixture which, based on the molar amount of the $C_3$ precursor compound present therein, comprises $\geq 200$ molar ppm of $C_2$ compounds is used for the partial heterogeneously catalyzed gas phase oxidation of a $C_3$ precursor compound.
19. The process according to any one of embodiments 1 to 17, wherein a starting reaction gas mixture which, based on the molar amount of the $C_3$ precursor compound present therein, comprises $\geq 300$ molar ppm of $C_2$ compounds is used for the partial heterogeneously catalyzed gas phase oxidation of a $C_3$ precursor compound.
20. The process according to any one of embodiments 1 to 17, wherein a starting reaction gas mixture which, based on the molar amount of the $C_3$ precursor compound present therein, comprises $\geq 400$ molar ppm of $C_2$ compounds is used for the partial heterogeneously catalyzed gas phase oxidation of a $C_3$ precursor compound.
21. The process according to any one of embodiments 1 to 17, wherein a starting reaction gas mixture which, based on the molar amount of the $C_3$ precursor compound present therein, comprises $\geq 500$ molar ppm of $C_2$ compounds is used for the partial heterogeneously catalyzed gas phase oxidation of a $C_3$ precursor compound.
22. The process according to any one of embodiments 1 to 17, wherein a starting reaction gas mixture which, based on the molar amount of the $C_3$ precursor compound present therein, comprises $\geq 750$ molar ppm of $C_2$ compounds is used for the partial heterogeneously catalyzed gas phase oxidation of a $C_3$ precursor compound.

23. The process according to any one of embodiments 1 to 17, wherein a starting reaction gas mixture which, based on the molar amount of the $C_3$ precursor compound present therein, comprises $\geq 1000$ molar ppm of $C_2$ compounds is used for the partial heterogeneously catalyzed gas phase oxidation of a $C_3$ precursor compound.

24. The process according to any one of embodiments 1 to 17, wherein a starting reaction gas mixture which, based on the molar amount of the $C_3$ precursor compound present therein, comprises $\geq 1500$ molar ppm of $C_2$ compounds is used for the partial heterogeneously catalyzed gas phase oxidation of a $C_3$ precursor compound.

25. The process according to any one of embodiments 18 to 24, wherein the starting reaction gas mixture comprises from 4 to 20% by volume of $C_3$ precursor compound.

26. The process according to any one of embodiments 18 to 25, wherein the starting reaction gas mixture comprises $\geq 1\%$ by weight of water vapor.

27. The process according to any one of embodiments 18 to 25, wherein the starting reaction gas mixture comprises $\geq 2\%$ by weight of water vapor.

28. The process according to any one of embodiments 18 to 25, wherein the starting reaction gas mixture comprises $\geq 3\%$ by weight of water vapor.

29. The process according to any one of embodiments 18 to 25, wherein the starting reaction gas mixture comprises $\geq 5\%$ by weight of water vapor.

30. The process according to any one of embodiments 18 to 25, wherein the starting reaction gas mixture comprises $\geq 7\%$ by weight of water vapor.

31. The process according to any one of embodiments 1 to 30, wherein the liquid phase P has been obtained from the product gas mixture of the partial heterogeneously catalyzed gas phase oxidation by employing at least one noncrystallizative thermal separation process.

32. The process according to embodiment 31, wherein the at least one noncrystallizative thermal separation process comprises at least one separation process from the group comprising absorption, partial condensation, fractional condensation, rectification, stripping and desorption.

33. The process according to embodiment 31 or 32, wherein mother liquor which comprises enriched glyoxal and remains in the course of crystallization is recycled into at least one of the noncrystallizative thermal separation processes.

34. The process according to embodiment 33, wherein mother liquor which comprises enriched glyoxal and remains in the course of crystallization is recycled into a fractional condensation of the product gas mixture of the heterogeneously catalyzed gas phase oxidation.

35. The process according to any one of embodiments 1 to 34, wherein the crystallizative separation is undertaken by means of a suspension crystallization.

36. The process according to embodiment 35, wherein suspension crystals formed in the course of suspension crystallization and remaining mother liquor are separated from one another by means of a wash column.

37. The process according to embodiment 36, wherein the suspension crystals are washed in the wash column with the melt of acrylic acid crystals removed beforehand in the wash column.

38. The process according to any one of embodiments 1 to 37, which comprises the following process steps:
   a. crystallizing acrylic acid out of the liquid phase P;
   b. separating the acrylic acid crystals from mother liquor which remains in the course of crystallization;
   c. at least partly melting the acrylic acid crystals removed in step b);
   d. at least partly recycling the molten acrylic acid crystals from step c) to step b) and/or step a).

39. The process according to any one of embodiments 1 to 38, wherein the liquid phase P, based on acrylic acid present therein, comprises from 0.2 to 30% by weight of water.

40. The process according to any one of embodiments 1 to 39, wherein the liquid phase P is obtained by transferring acrylic acid present and glyoxal present in the product gas mixture to an aqueous liquid phase, and removing at least a portion of the water from this liquid aqueous phase by means of azeotropic rectification, which leaves the liquid phase P.

41. The process according to any one of embodiments 1 to 40, wherein the liquid phase P comprises the glyoxal in the form of monomeric glyoxal monohydrate and/or monomeric glyoxal dihydrate to an extent of more than 50 mol %.

42. The process according to any one of embodiments 1 to 40, wherein the liquid phase P comprises the glyoxal in the form of monomeric glyoxal monohydrate and/or monomeric glyoxal dihydrate to an extent of more than 70 mol %.

43. The process according to any one of embodiments 1 to 40, wherein the liquid phase P comprises the glyoxal in the form of monomeric glyoxal monohydrate and/or monomeric glyoxal dihydrate to an extent of more than 90 mol %.

44. The process according to any one of embodiments 1 to 43, wherein the product gas mixture, based on the molar amount of acrylic acid present therein, comprises at least 200 molar ppm of glyoxal.

45. The process according to any one of embodiments 1 to 43, wherein the product gas mixture, based on the molar amount of acrylic acid present therein, comprises at least 400 molar ppm of glyoxal.

46. The process according to any one of embodiments 1 to 43, wherein the product gas mixture, based on the molar amount of acrylic acid present therein, comprises at least 750 molar ppm of glyoxal.

47. The process according to any one of embodiments 1 to 46, wherein, in the course of obtaining the liquid phase P, acrylic acid present in the product gas mixture is transferred to the condensed (e.g. liquid) phase while residual gas remaining in gaseous form is recycled at least partly into the partial heterogeneously catalyzed gas phase oxidation of the $C_3$ precursor compound.

48. The process according to any one of embodiments 1 to 47, which is followed by a process in which acrylic acid crystals are melted and free-radically polymerized into at least one polymer.

EXAMPLES

I. Detection of the above-average promotion of the undesired free-radical polymerization of acrylic acid by monomeric glyoxal in acrylic acid 1. Preparation of a solution of monomeric glyoxal in anhydrous methanol 2.0 g of finely divided glyoxal trimer dihydrate (from Fluka, purity >95%) and 5.0 g of finely divided $P_2O_5$ (from Aldrich, purity >98%) were mixed homogeneously. Subsequently, the mixture was heated to 180° C. at a pressure of <50 mbar, and the gaseous stream composed of monomeric glyoxal with or without minor traces of water vapor which evolved continuously was passed over finely divided $P_2O_5$ (binds the residual traces of water vapor) into anhydrous methanol (from Aldrich, purity >99.8%).

Based on the starting amount of methanol, 0.3% by weight of monomeric glyoxal was introduced and dissolved in the methanol (cf. also Y. Chen, L. Zhu in "Wavelength-Dependent Photolysis of Glyoxal in the 290-420 nm Region", J. Phys. Chem. A, 2003, 107, 4643-4651). The resulting methanolic solution is referred to hereinafter as solution M (the corresponding thermally labile acetals are formed from the glyoxal and methanol in the methanolic solution and redissociate back to monomeric glyoxal and methanol at moderately elevated temperature).

2. Preparation of glacial acrylic acids doped with small amounts of different possible by-product aldehydes 5 indistinguishable samples (each of 0.5 ml) of glacial acrylic acid were prepared. To this end, glacial acrylic acid storage-stabilized with the monomethyl ether of hydroquinone (MEHQ) was distilled over freshly under reduced pressure and stabilized with 10 ppm by weight of phenothiazine (PTZ).

The purity of the glacial acrylic acid samples thus obtained was >99.8% by weight with a total aldehyde and ketone content of <10 ppm by weight. The samples were stored in the frozen state.

Subsequently, the samples were doped by weighing in the appropriate aldehydes as follows (in the case of glyoxal, the solution M was used for this purpose; the molar ppm are always based on the molar amount of acrylic acid present; owing to the methanol content of the solution M, an appropriate amount of methanol was additionally used for doping in the case of doping with aldehydes other than glyoxal):

sample 1: 86 molar ppm of monomeric glyoxal
sample 2: 96 molar ppm of benzaldehyde
sample 3: 166 molar ppm of formaldehyde
sample 4: 104 molar ppm of 2-furfural
sample 5: 113 molar ppm of acetaldehyde Identical glass ampoules with a capacity of in each case 1.8 ml were sealed by melting under an air atmosphere, and the ampoules were each, immediately after they had been finished, stored at a temperature of 120° C. in a forced-air drying cabinet with rotation in order to ensure full mixing. Then the time T until complete polymerization of the particular sample was detected visually.

The test series was repeated three times and the measurements were averaged arithmetically. The mean results for the time T of the particular samples were:

sample 1: 117 min
sample 2: 222 min
sample 3: 197 min
sample 4: 199 min
sample 5: 174 min The results obtained indicate the exceptional position of monomeric glyoxal.

II. Inventive crystallizative removal

1. A gaseous stream of monomeric glyoxal as obtained in 1.1. was introduced into glyoxal-free acrylic acid with the following impurities (the data are based on gas chromatography analysis; the water determination was effected according to Karl-Fischer, and the PTZ analysis by wet-chemical means)

37 ppm by weight of allyl acrylate,
3319 ppm by weight of benzaldehyde,
3404 ppm by weight of diacrylic acid,
1.94% by weight of acetic acid,
0.91% by weight of propionic acid,
4211 ppm by weight of furfural-2 (furan-2-aldehyde),
33 ppm by weight of furfural-3 (furan-3-aldehyde),
348 ppm by weight of water, and
297 ppm by weight of phenothiazine, and an acrylic acid content of 95.80% by weight, until it had been doped, based on the amount of acrylic acid present, with 1741 molar ppm of monomeric glyoxal (=1277 ppm by weight based on the total weight of the contaminated acrylic acid).

Subsequently, it was fed at a flow rate of 135 kg/h and a temperature of 17.3° C. to a cooling disk crystallizer (with a liquid capacity of approx. 95 liters) with wiped cooling disks.

The crystallizer had 7 spherical cooling disks arranged suspended in succession at an equidistant interval of 12 cm in a trough.

The diameter of the cooling disks was 32 cm and the disk thickness was 15 mm with a wall thickness of 2.5 mm. The cooling surfaces were manufactured from stainless steel (DIN material 1.4571). A water-glycol mixture as the coolant (353 l/h) (55% by volume of water, 45% by volume of glycol) flowed through the cooling disks. The coolant flowed into the first cooling disk with an inlet temperature of 2.5° C. and left the last cooling disk with an outlet temperature of 8.6° C. The doped acrylic acid and the coolant were conducted in countercurrent through the crystallizer. The unwiped edges of the cooling disks were trace-heated by a hollow profile surrounding them (hose-type tube with an external diameter of 12 mm), in order to prevent encrustation with crystals. For this purpose, the same water-glycol mixture, but having an entrance temperature of 24° C., flowed in parallel through the hollow profiles of the cooling disks in a total amount of 51 l/h. The wipers of the cooling plates were driven at a speed of 26 rpm by means of a horizontal shaft. The crystal suspension obtained in the crystallizer left it with a temperature of 10.6° C.

A flow rate of 119 kg/h of acrylic acid crystal suspension was withdrawn from the crystallizer via a coarse screen (mesh size approx. 3 mm; the coarse screen pursued the purpose of retaining relatively coarse crystal agglomerates formed in the crystallizer, since these could cause blockage of the suspension feed line to the wash column) with a temperature of 10.6° C. and pumped into a hydraulic wash column from the top. This column consisted of a circular cylindrical jacketed glass vessel (height: 1000 mm; external diameter of the inner cylinder: 100 mm, wall thickness of the inner cylinder: 9 mm; the outer cylinder was sealed around the inner cylinder with the aid of corresponding seals; the intermediate space was filled with air; external diameter of the outer cylinder: 130 mm; wall thickness of the outer cylinder: 5 mm). Suspended centrally within the inner cylinder was a metallic filter tube (made of stainless steel (DIN material 1.4571)) which had an external diameter of 20 mm and a wall thickness of 1.6 mm. A cylindrical filter of height 40 mm and external diameter 20 mm was inserted into the filter tube with its lower edge 200 mm above the lower end of the glass jacket, and the liquid phase present in the acrylic acid crystal suspension was removed through it. By virtue of removal of the aforementioned liquid phase, a crystal bed was obtained around the filter tube in the glass cylinder, the bed length (height) of which was kept at a value of 510 mm (measured from the lower end of the glass jacket) with the aid of optical height measurement. To control the bed height, a control stream of about 95 kg/h of liquid phase removed via the filter tube was recycled into the wash column at the top thereof. At the lower end of the glass cylinder, the washed crystal bed was removed with a rotating bladed disk (30 rpm), and the crystals removed are pumped in circulation and melted in a melt circuit consisting of pump, heater, inhibitor metering point and appropriate pipelines. The inhibitor was metered in in the form of PTZ dissolved in pure melt, such that the PTZ content of the melt circuit was approx. 200 ppm by weight. The temperature in the melt circuit upstream of the pure melt recycling into the lower end of the wash column, which is required for crystal washing, was 18° C.

Only about 5.5 kg/h of molten crystals were withdrawn from the melt circuit as purified product (residual melt). The flow rate of pure product withdrawn from the melt circuit was regulated such that a wash front formed in the crystal bed, visible externally at a level of from about 90 to 1 10 mm above the lower end of the glass cylinder. To regulate the flow rate of the pure melt withdrawn from the melt circuit, the temperature in the crystal bed at a level of 1 00 mm above the lower end of the glass cylinder was employed, which was regulated by closed-loop control to a value of 11.5° C. by the actuation of a valve in the pure melt withdrawal line (adjustment of the withdrawal flow rate).

The analysis of the liquid phase (mother liquor) conducted out of the filter tube showed a glyoxal content of 1365 ppm by weight (based on the weight of the mother liquor).

The analysis of the molten crystals withdrawn from the melt circuit showed a glyoxal content of less than 0.1 ppm by weight (based on the crystal weight). A depletion coefficient of $A^{Gly} > 13650$ is thus calculated from the two values above.

2. Experiment II.1. was repeated, except that the glyoxal doping was undertaken with an aqueous solution which was purchased from Aldrich, stored at 25° C. and, according to in-house analysis, comprised glyoxal to an extent of 40% of its weight (calculated as monomeric glyoxal). The doping of the acrylic acid was accompanied by slight formation of precipitate, which is presumably attributable to high molecular weight polyglyoxals (or hydrates thereof) which are sparingly soluble in the acrylic acid. The mixture was therefore filtered and the filtrate obtained was acrylic acid doped with 1877 molar ppm of glyoxal. This was used to follow the procedure in experiment II.1. The depletion coefficient $A^{Gly}$ (calculated as monomeric glyoxal) thus determined experimentally was >14 720.

U.S. Provisional Patent Applications No. 61/084109, filed Jul. 28, 2008, and No. 61/091900, filed Aug. 26, 2008, are incorporated into the present patent application by literature reference. With regard to the abovementioned teachings, numerous changes and deviations from the present invention are possible. It can therefore be assumed that the invention, within the scope of the appended claims, can be performed differently from the way described specifically herein.

The invention claimed is:

1. A process for separating acrylic acid present as a main product and glyoxal present as a by-product in a product gas mixture of a partial heterogeneously catalyzed gas phase oxidation of a $C_3$ precursor compound of acrylic acid, in which a liquid phase P is obtained which comprises acrylic acid to an extent of at least 70% of its weight and, based on the molar amount of acrylic acid present therein, comprises at least 200 molar ppm of glyoxal, which comprises separating the glyoxal from the acrylic acid in the liquid phase P by crystallization, the acrylic acid being enriched in the crystals formed and the glyoxal in the mother liquor which remains in the course of crystallization.

2. The process according to claim 1, wherein the liquid phase P, based on the molar amount of acrylic acid present therein, comprises at least 300 molar ppm of glyoxal.

3. The process according to claim 1, wherein the liquid phase P, based on the molar amount of acrylic acid present therein, comprises at least 400 molar ppm of glyoxal.

4. The process according to claim 1, wherein the liquid phase P, based on the molar amount of acrylic acid present therein, comprises at least 500 molar ppm of glyoxal.

5. The process according to claim 1, wherein the liquid phase P, based on the molar amount of acrylic acid present therein, comprises at least 1000 molar ppm of glyoxal.

6. The process according to claim 1, wherein the liquid phase P, based on the molar amount of acrylic acid present therein, comprises at least 1500 molar ppm of glyoxal.

7. The process according to any one of claims 1 to 6, wherein the liquid phase P comprises acrylic acid to an extent of at least 75% of its weight.

8. The process according to any one of claims 1 to 6, wherein the liquid phase P comprises acrylic acid to an extent of at least 80% of its weight.

9. The process according to any one of claims 1 to 6, wherein the liquid phase P comprises acrylic acid to an extent of at least 85% of its weight.

10. The process according to any one of claims 1 to 6, wherein the liquid phase P comprises acrylic acid to an extent of at least 90% of its weight.

11. The process according to any one of claims 1 to 6, wherein the liquid phase P comprises acrylic acid to an extent of at least 95% of its weight.

12. The process according to any one of claims 1 to 6, wherein the liquid phase P comprises acrylic acid to an extent of at least 96% of its weight.

13. The process according to any one of claims 1 to 6, wherein the liquid phase P comprises acrylic acid to an extent of at least 97% of its weight.

14. The process according to claim 1, wherein the $C_3$ precursor compound is propylene.

15. The process according to claim 1, wherein the $C_3$ precursor compound is acrolein.

16. The process according to claim 1, wherein the $C_3$ precursor compound is propane.

17. The process according to claim 1, wherein the $C_3$ precursor compound is glycerol.

18. The process according to claim 1, wherein a starting reaction gas mixture which, based on the molar amount of the $C_3$ precursor compound present therein, comprises $\geq 200$ molar ppm of $C_2$ compounds is used for the partial heterogeneously catalyzed gas phase oxidation of a $C_3$ precursor compound.

19. The process according to claim 1, wherein a starting reaction gas mixture which, based on the molar amount of the $C_3$ precursor compound present therein, comprises $\geq 300$ molar ppm of $C_2$ compounds is used for the partial heterogeneously catalyzed gas phase oxidation of a $C_3$ precursor compound.

20. The process according to claim 1, wherein a starting reaction gas mixture which, based on the molar amount of the $C_3$ precursor compound present therein, comprises $\geq 400$ molar ppm of $C_2$ compounds is used for the partial heterogeneously catalyzed gas phase oxidation of a $C_3$ precursor compound.

21. The process according to claim 1, wherein a starting reaction gas mixture which, based on the molar amount of the $C_3$ precursor compound present therein, comprises 500 molar ppm of $C_2$ compounds is used for the partial heterogeneously catalyzed gas phase oxidation of a $C_3$ precursor compound.

22. The process according to claim 1, wherein a starting reaction gas mixture which, based on the molar amount of the $C_3$ precursor compound present therein, comprises $\geq 750$ molar ppm of $C_2$ compounds is used for the partial heterogeneously catalyzed gas phase oxidation of a $C_3$ precursor compound.

23. The process according to claim 1, wherein a starting reaction gas mixture which, based on the molar amount of the $C_3$ precursor compound present therein, comprises $\geq 1000$ molar ppm of $C_2$ compounds is used for the partial heterogeneously catalyzed gas phase oxidation of a $C_3$ precursor compound.

24. The process according to claim 1, wherein a starting reaction gas mixture which, based on the molar amount of the $C_3$ precursor compound present therein, comprises $\geq 1500$ molar ppm of $C_2$ compounds is used for the partial heterogeneously catalyzed gas phase oxidation of a $C_3$ precursor compound.

25. The process according to claim 18, wherein the starting reaction gas mixture comprises from 4 to 20% by volume of $C_3$ precursor compound.

26. The process according to claim 18, wherein the starting reaction gas mixture comprises $\geq 1\%$ by weight of water vapor.

27. The process according to claim 18, wherein the starting reaction gas mixture comprises $\geq 2\%$ by weight of water vapor.

28. The process according to claim 18, wherein the starting reaction gas mixture comprises $\geq 3\%$ by weight of water vapor.

29. The process according to claim 18, wherein the starting reaction gas mixture comprises $\geq 5\%$ by weight of water vapor.

30. The process according to claim 18, wherein the starting reaction gas mixture comprises $\geq 7\%$ by weight of water vapor.

31. The process according to claim 1, wherein the liquid phase P has been obtained from the product gas mixture of the partial heterogeneously catalyzed gas phase oxidation by employing at least one noncrystallizative thermal separation process.

32. The process according to claim 31, wherein the at least one noncrystallizative thermal separation process comprises at least one separation process comprising absorption, partial condensation, fractional condensation, rectification, stripping or desorption.

33. The process according to claim 31 or 32, wherein mother liquor which comprises enriched glyoxal and remains in the course of crystallization is recycled into at least one of the noncrystallizative thermal separation processes.

34. The process according to claim 33, wherein mother liquor which comprises enriched glyoxal and remains in the course of crystallization is recycled into a fractional condensation of the product gas mixture of the heterogeneously catalyzed gas phase oxidation.

35. The process according to claim 1, wherein the crystallizative separation is undertaken by a suspension crystallization.

36. The process according to claim 35, wherein suspension crystals formed in the course of suspension crystallization and remaining mother liquor are separated from one another by a wash column.

37. The process according to claim 36, wherein the suspension crystals are washed in the wash column with the melt of acrylic acid crystals removed beforehand in the wash column.

38. The process according to claim 1, which comprises the following sub-processes:
  a) crystallizing acrylic acid out of the liquid phase P;
  b) separating the acrylic acid crystals from mother liquor which remains in the course of crystallization;
  c) at least partly melting the acrylic acid crystals removed in b);
  d) at least partly recycling the molten acrylic acid crystals from c) to b) and/or a).

39. The process according to claim 1, wherein the liquid phase P, based on acrylic acid present therein, comprises from 0.2 to 30% by weight of water.

40. The process according to claim 1, wherein the liquid phase P is obtained by transferring acrylic acid present and glyoxal present in the product gas mixture to an aqueous liquid phase, and removing at least a portion of the water from this liquid aqueous phase by azeotropic rectification, which leaves the liquid phase P.

41. The process according to claim 1, wherein the liquid phase P comprises the glyoxal in the form of monomeric glyoxal monohydrate and/or monomeric glyoxal dihydrate to an extent of more than 50 mol %.

42. The process according to claim 1, wherein the liquid phase P comprises the glyoxal in the form of monomeric glyoxal monohydrate and/or monomeric glyoxal dihydrate to an extent of more than 70 mol %.

43. The process according to claim 1, wherein the liquid phase P comprises the glyoxal in the form of monomeric glyoxal monohydrate and/or monomeric glyoxal dihydrate to an extent of more than 90 mol %.

44. The process according to claim 1, wherein the product gas mixture, based on the molar amount of acrylic acid present therein, comprises at least 200 molar ppm of glyoxal.

45. The process according to claim 1, wherein the product gas mixture, based on the molar amount of acrylic acid present therein, comprises at least 400 molar ppm of glyoxal.

46. The process according to claim 1, wherein the product gas mixture, based on the molar amount of acrylic acid present therein, comprises at least 750 molar ppm of glyoxal.

47. The process according to claim 1, wherein, in the course of obtaining the liquid phase P, acrylic acid present in the product gas mixture is transferred to the condensed phase while residual gas remaining in gaseous form is recycled at least partly into the partial heterogeneously catalyzed gas phase oxidation of the $C_3$ precursor compound.

48. The process according to claim 1, which is followed by a process in which acrylic acid crystals are melted and free-radically polymerized into at least one polymer.

* * * * *